US006514980B1

(12) United States Patent
Boyd

(10) Patent No.: US 6,514,980 B1
(45) Date of Patent: Feb. 4, 2003

(54) NUCLEOSIDE ANALOGS IN COMBINATION THERAPY OF HERPES SIMPLEX INFECTIONS

(75) Inventor: Malcolm Richard Boyd, Epsom (GB)

(73) Assignee: Novartis International Pharmaceutical Ltd., Hamilton (BM)

( * ) Notice: Subject to any disclaimer, the term of this patent is extended or adjusted under 35 U.S.C. 154(b) by 0 days.

(21) Appl. No.: 09/626,015

(22) Filed: Jul. 26, 2000

Related U.S. Application Data

(62) Division of application No. 09/117,154, filed on Jul. 24, 1998, now abandoned.

(30) Foreign Application Priority Data

Jan. 26, 1996 (GB) .............................. 9601544

(51) Int. Cl.[7] ........................ A61K 31/522; A61K 31/56

(52) U.S. Cl. .................. 514/263.31; 514/171; 514/177; 514/178; 514/179; 514/262.1; 514/263.3; 514/264.1; 514/105; 514/931; 514/934

(58) Field of Search ................................ 514/261, 262, 514/264.1, 26, 177, 178, 171, 179, 262.1, 105, 263.3, 263.31; 424/177.1

(56) References Cited

U.S. PATENT DOCUMENTS

| 3,317,384 A | 5/1967 | Underwood et al. ........... 167/58 |
| 5,508,310 A | 4/1996 | Rhodes ........................ 514/576 |
| 6,136,835 A | * 10/2000 | Camden |

FOREIGN PATENT DOCUMENTS

| GB | 1 099 385 | 1/1968 |
| WO | WO 91/11187 | 8/1991 |
| WO | WO 92/00742 | 1/1992 |
| WO | WO 96/19482 | 6/1996 |
| WO | WO 96/24355 | 8/1996 |

OTHER PUBLICATIONS

McKeough et al., "Combination of Peroral Famciclovir and a Topical Cortocosteroid for the Treatment of Experimental Ultraviolet Radiation (UVR)–Indiced Herpes Labialis: A Double–Blind, Placebo–Controlled Trial.", 39th Annual ICAAC, San Francisco, CA, Abstracts 1408 (1999).

Awan et al., "Combinations of Antiviral and Anti–Inflammatory Preparations for the Topical Treatment of Herpes Simplex Virus Assessed Using a Murine Zosteriform Infection Model", Antiviral Chemistry & Chemotherapy, vol. 9, pp. 19–24 (1998).

Thackray et al., "The Influence of Cyclosporin Immunosuppression on the Efficacy of Famciclovir or Valaciclovir Chemotherapy studied in a Murine Herpes Simplex Virus Type 1 Infection Model", vol. 8, No. 4, pp. 317–326 (1997).

Field et al., "Can Herpes Simplex Virus Latency be Prevented Using Conventional Nucleoside Analogue Chemotherapy?", Antiviral Chemistry & Chemotherapy, vol. 8, Suppl. 1, pp. 59–66 (1997).

Murakami et al., "Bell Palsy and Herpes Simplex Virus: Identification of Viral DNA in Endoneurial Fluid and Muscle", Ann. Intern. Med., vol. 124, No. 1, Pt. 1, pp 27–30 (1996).

Baringer, "Herpes Simplex Virus and Bell Palsey", Ann. Intern. Med., vol. 124, No. 1, Pt. 1, pp 63–65 (1996).

Field et al., "Effects of Cyclosporin Immunosuppression on the Efficacy of Antiviral Chemotherapy Studied in a Murine Infection Model for HSV–1.", Clin Vet. Med., pp. 1–11 (1996).

Field et al., ECC GlasGow Presentation, Abstract, May 1996.

"ЛЕКАРСТВЕННЫЕ СРЕДТВА ,(Пособие для врачей)", , Часть II, Москва "Медицина",, pp. 192–193, 206–207 (1993).

Choi et al., "Enhanced Transdermal Delivery of Propranolol, Hydro–Cortisone, Acyclovir and Peptide–Type Drugs.", Dissertation Abstracts International, vol. 50, No. 8, pp 3422–B (1990).

Peters, "Immunological Aspects of Antiviral Therapy", Sprinter Semin. Immunopathol., vol. 12, pp. 47–56 (1990).

Hilfenhaus et al., "Combined Antiviral Effects of Acyclovir or Bromovinyldeoxyuridine and Human Immunoglobulin in Herpes Simplex Virus–Infected Mice", Antiviral Research, vol. 7, pp. 227–235 (1987).

Schinazi et al., "Studies in vitro and in vivo of Combinations of Antivirals and Anti–inflammatory Agents in Relation to the Treatment of Herpes Simplex Viruses," Chemical Abstract, 97:156002r, Curr. Chemother. Immunother., Proc. Int. Congr. Chemother., 12th, 1981 (Publ. 1982). 2, pp. 1085–1087.

Ikeda et al., "Antiherpes Activity of Chemically Synthesized Lipid A–subunit Analogue GLA–60 in Immunosuppressed Mice, "Antiviral Research, vol. 11, pp. 173–180 (1989).

Nomura et al., "Two Cases of Encephalo–Myelo–Radiculoneuropathy, Triggered by Herpes Simplex Virus Type–1 Infection," Abstract (Medline), Clinical Neurology, vol. 37(7) pp. 621–625 (1997).

Field et al., "Comparison of Efficacies of Famciclovir and Valaciclovir against Herpes Simplex etc.," Antimicrobial Agents and Chemotherapy, vol. 39(5), pp. 1114–1119 (1995).

Field et al., "The Effects of Delayed–Onset Chemotherapy Using Famciclovir or Valaciclovir etc.," Antiviral Chemistry & Chemotherapy, vol. 6(4) pp. 210–216 (1995).

* cited by examiner

Primary Examiner—James O. Wilson
(74) Attorney, Agent, or Firm—Thomas R. Savitsky

(57) ABSTRACT

A pharmaceutical product comprising a nucleoside analogue active against herpes simplex virus, such as acyclovir/valaciclovir or penciclorivir/famciclovir, and an immunosuppressant, as a combined preparation for simultaneous, separate or sequential use in the treatment and/or prevention of herpes simplex virus infections.

12 Claims, No Drawings

NUCLEOSIDE ANALOGS IN COMBINATION THERAPY OF HERPES SIMPLEX INFECTIONS

This is a division of application Ser. No. 09/117,154, filed Jul. 24, 1998, now abandoned.

This invention relates to the use of a nucleoside analogue active against herpes simplex virus (HSV), in the treatment of herpes simplex virus infections, and to pharmaceutical compositions containing the two components.

The disease indication for herpes simplex subtype 1 (HSV-1) is herpes labialis (cold sores), and the disease indication for herpes simplex subtype 2 (HSV-2) is genital herpes.

Herpes Labialis is a common world-wide disease characterized by repeated attacks of versicular eruptions most commonly recognised on the lips and perioral skin. Many patients report pain, swelling and significant cosmetic concerns associated with subsequent ulceration of lesions. Although generally a minor disease, in some patients the consequences of frequent severe attacks can be debilitating. The disease is naturally self-limiting in immunecompetent individuals and recurrent episodes last 7–10 days.

First infection with genital herpes may be severe (primary first episode) if the patient has no previous history of labial or genital herpes infection, while a less severe disease occurs if any antibody response is developed through previous exposure to HSV—non-primary first episode. The most common sequel to primary genital herpes infection is recurrent disease. The attack rate varies greatly but is likely that patients will experience on average 4–5 episodes per year. Symptomatology in these episodes are characterised by painful lesions which progress from papules and vesicles through to ulcers and finally crusts. Lesions may be accompanied by a range of symptoms including pain, tenderness, itching and swelling of the affected area.

EP-A-141927 (Beecham Group p.l.c.) discloses penciclovir, the compound of formula (A):

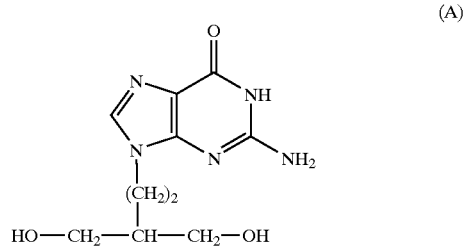

(A)

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V11-5 p.193 of 'Abstracts of 14th Int. Congress of Microbiology', Manchester, England Sep. 7–13, 1986 (Boyd et. al.).

Orally active bioprecursors of the compound of formula (A) are of formula (B):

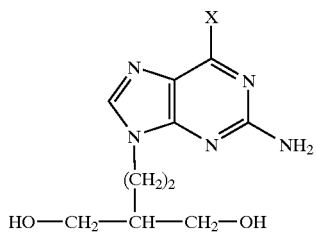

(B)

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are in the form of the acetyl derivative, described in Example 2 of EP-A-182024, hereinafter referred to as famciclovir.

The compounds of formulae (A) and (B) and salts and derivatives thereof have been described as useful in the treatment of infections caused by herpesviruses, such as herpes simplex type 1 and herpes simplex type 2. All references herein to penciclovir/famciclovir include pharmaceutically acceptable salts, such as the hydrochloride, and solvates, such as hydrates.

When used herein the term 'immunosuppressant' includes pharmaceutical agents such as cytotoxic agents such as cyclophosphamide and cyclosporin A and corticosteroids such as hydrocortisone and dexamethasone and non steroidal antiinflammatory agents.

In one preferred aspect, the immunosuppressant is cyclosporin A.

The anti-herpes simplex virus properties of nucleoside analogues such as penciclovir/famciclovir or ayclovir/valaciclovir are potentially enhanced by administering the compound in conjunction with an immunosuppressant. The rationale is that in mice infected with herpes simplex virus, treatment with an antiviral agent to achieve clearance of the virus is particularly effective when the mice are immunosuppressed with cyclosporin A.

Accordingly, the present invention provides a pharmaceutical product comprising a nucleoside analogue active against herpes simplex virus, such as acyclovir/valaciclovir or penciclovir/famciclovir, and an immunosuppressant, as a combined preparation for simultaneous, separate or sequential use in the treatment and/or prevention of herpes simplex virus infections.

The present invention also provides a method of treatment and/or prophylaxis of herpes simplex virus infections, which comprises administering to a human or animal subject, a nucleoside analogue active against herpes simplex virus, such as acyclovir/valaciclovir or penciclovir/famciclovir, and an immunosuppressant or a pharmaceutically acceptable salt or ester thereof.

The invention further provides the use of a nucleoside analogue antiviral active against herpes simplex virus, such as acyclovir/valaciclovir or penciclovir/famciclovir for the manufacture of a medicament for administration in conjunction with an immunosuppressant or a pharmaceutically acceptable salt or ester thereof, for the treatment and/or prevention of herpes simplex virus infections.

Co-administration of penciclovir/famciclovir with an immunosuppressant is particularly useful for the treatment of severe and/or prolonged herpes simplex virus infections.

The antiviral such as penciclovir/famciclovir and the immunosuppressant or a pharmaceutically acceptable salt or ester thereof, may be administered as a single pharmaceutical composition comprising effective amounts of the two active ingredients. Alternatively the two active ingredients may be co-administered in the form of two separate pharmaceutical compositions for simultaneous or sequential use. Normally the active ingredients will be administered separately according to the normal dosage and administration regimen for the ingredients given alone. Commencement of administration may be either with the immunosuppressant or the antiviral.

The unit doses of the nucleside analogue may be administered, for example, 1 to 4 times per day. The exact dose will depend on the route of administration and the severity of the condition being treated, and it will be appreciated that it may be necessary to make routine variations to the dosage depending on the age and weight of the patient and immunocompromised patients may require an increased dosage.

Immunosuppressants are administered according to the conventional route of administration for the immunosuppressant employed.

When the two active ingredients are administered as separate preparations, they are preferably given enterally, such as orally or parenterally (e.g. intramuscularly or, more particularly, intravenously).

According to a further aspect the invention provides a pharmaceutical composition, for use in human or veterinary medicine, comprising a nucleoside analogue active against herpes simplex virus, such as acyclovir/valaciclovir or penciclovir/famciclovir, and an immunosuppressant or a pharmaceutically acceptable salt or ester thereof.

Compositions according to the invention may be formulated in conventional manner using one or more physiologically acceptable carriers or excipients. Thus the compositions may, for example, be formulated for oral, buccal, parenteral or rectal administration. Compositions for administration by the oral route, in the form of for example tablets or capsules, are preferred.

Compositions for oral use such as tablets and capsules may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricant (e.g. magnesium stearate, talc or silica); disintegrants (e.g. potato starch or sodium starch glycollate); or wetting agent (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of one or both active ingredients.

For parenteral administration the compositions may be presented in a form suitable for bolus injection or continuous infusion. Formulations for injection may be presented in unit dosage form e.g. in syringes, ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredients may be in powder form for constitution with a suitable vehicle, e.g. sterile pyrogen-free water, before use.

For rectal administration the compositions may be formulated as suppositories or retention enemas, e.g. containing conventional suppository bases such as cocoa butter or other glycerides.

The topical route of administration is preferred for treatment of herpes labialis and cream formulations are suitable, such as that descibed for penciclovir in WO 91/11187 (Beecham Group p.l.c.).

The pharmaceutical compositions of the invention may be prepared according to conventional techniques well known in the pharmaceutical industry. Thus, for example, the penciclovir/famciclovir and the immunosuppressant may be admixed together, if desired, with suitable excipients. Tablets may be prepared, for example, by direct compression of such a mixture. Capsules may be prepared by filling the blend along with suitable excipients into gelatin capsules, using a suitable filling machine. Controlled release forms for oral or rectal administration may be formulated in a conventional manner associated with controlled release forms. Creams and other formulations for topical administration are formulated in conventional manner.

The compositions for use according to the invention may, if desired, be presented in a pack or dispenser device which may contain one or more unit dosage forms containing the active ingredients. The pack may for example comprise metal or plastic foil, such as a blister pack. The pack or dispenser device may be accompanied by instructions for administration. Where the penciclovir/famciclovir and the immunosuppressant are intended for administration as two separate compositions these may be presented in the form of, for example, a twin pack.

It will be appreciated that an alternative anti-herpes simplex virus nucleoside analogue such as ganciclovir, may be used in place of acyclovir/valaciclovir or penciclovir/famciclovir in the present invention, at an appropriate dosage level according to its activity.

Information with respect to structure and activity of nucleoside analogues hereinbefore may be obtained from well known pharmaceutical industry references, such as "Pharmaprojects", PJB publications Limited, Richmond, Surrey, U.K. or from 'R & D Focus', isssued by IMS World publications, 364 Euston Road, London NW1 3BL.

References to a anti-herpes simplex virus nucleoside analogue, including compounds described in the abovementioned patent references and the specific compounds mentioned hereinbefore and salts thereof, include solvates such as hydrates.

Examples of pharmaceutically acceptable salts are as described in the aforementioned Patent references in the name of Beecham Group p.l.c. and references quoted therein, the subject matter of which are incorporated herein by reference.

Anti-herpes simplex virus nucleoside analogues may be identified by standard methods.

The following results from animal studies illustrate the invention.

EXPERIMENTS IN MICE INFECTED WITH HSV-1 VIRUS

A cutaneous infection was established by inoculation of the ear pinnae of mice with HSV-1 (SC16) and the effects of oral famciclovir and valaciclovir on the latent virus infection was investigated.

BALB/c female mice (Bantin and Kingman, Kingston, Hull, UK) were purchased at 3 to 4 weeks old and inoculated one week later. Virus suspension (10 ul) containing 5×10$^4$ p.f.u. were inoculated into the skin of the left ear pinna. Skin thickness was measured daily in individual mice by means of an Engineers' micrometer screw gauge. (ref. Nash et al, 1980, J. Gen. Virol. 48, 351–357). Mice were killed daily and tissues removed for virus assays. Other mice were 4 months and then killed. The trigeminal ganglia and cervical dorsal root ganglia were removed and co-cultivated. Those cultures showing virus replication were recorded as positive.

In a first experiment, groups of immunocompetant mice were untreated (control), antiviral treatment was initiated on days 1, 2, 3, 4 or 5 post-infection (p.i.) and and ceased on day 10 p.i.. The compounds were administered ad libitum in the drinking water, at 1 mg/ml (approximately 100 mg/kg/day).

In a second experiment, mice were immunosupressed with Cyclosporin A (CyA) from day-2 to day=10 (day 0 being the day of infection). Groups of mice were untreated (control), or treated with famciclovir orally at 50 mg/kg twice daily from 22 h after infection to 55 or 10.5 days. The ganglia were examined for reactivation of infectious virus 1 or 4 months later.

The results show that in the second experiment, the effect of treating with famciclovir or valaciclovir has a significantly greater effect on virus replication and disease.

What is claimed is:

1. A pharmaceutical composition comprising an effective amount of a nucleoside analogue active against herpes simplex virus selected from the group consisting of acyclovir and valaciclovir, or a pharmaceutically acceptable salt or ester thereof and an effective amount of a pharmaceutically acceptable immunosuppressant.

2. A method of treatment or prophylaxis of herpes simplex virus infections in a human in need thereof, which method comprises administering to said human, an effective amount of a nucleoside analogue active against herpes simplex virus selected from the group consisting of acyclovir and valaciclovir, or a pharmaceutically acceptable salt or ester thereof and an effective amount of a pharmaceutically acceptable immunosuppressant.

3. The composition according to claim 1 wherein the immunosuppressant is a cytotoxic agent, a corticosteriod, or a non-steroidal anti-inflammatory agent.

4. The composition according to claim 1 wherein the immunosuppressant is a cyclophosphamide, cyclosporin A, hydrocortisone, or dexamethasone.

5. The method according to claim 2, wherein the immunosuppressant is a cytotoxic agent, a corticosteroid, or a non-steroidal anti-inflammatory agent.

6. The method according to claim 2, wherein the immunosuppressant is a cyclophosphamide, cyclosporin A, hydrocortisone, or dexamethasone.

7. A method of treatment or prophylaxis of a herpes simplex virus infection in a human in need thereof, which method comprises administering simultaneously to said human an effective amount of a nucleoside analogue active against herpes simplex virus selected from the group consisting of acyclovir and valaciclovir, or a pharmaceutically acceptable salt or ester thereof and an effective amount of a pharmaceutically acceptable immunosuppresant.

8. The method according to claim 7 wherein the immunosuppressant is a cytotoxic agent, a corticosteriod, or a non-steroidal anti-inflammatory agent.

9. The method according to claim 7 wherein the immunosuppressant is a cyclophosphamide, cyclosporin A, hydrocortisone, or dexamethasone.

10. A method of treatment or prophylaxis of a herpes simplex virus infection in a human in need thereof, which method comprises administering sequentially to said human an effective amount of a nucleoside analogue active against herpes simplex virus selected from the group consisting of acyclovir and valaciclovir, or a pharmaceutically acceptable salt or ester thereof and an effective amount of a pharmaceutically acceptable immunosuppresant.

11. The method according to claim 10 wherein the immunosuppressant is a cytotoxic agent, a corticosteriod, or a non-steroidal anti-inflammatory agent.

12. The method according to claim 10 wherein the immunosuppressant is a cyclophosphamide, cyclosporin A, hydrocortisone, or dexamethasone.

* * * * *

UNITED STATES PATENT AND TRADEMARK OFFICE
CERTIFICATE OF CORRECTION

PATENT NO. : 6,514,980 B1
DATED : February 4, 2003
INVENTOR(S) : Malcolm Richard Boyd It is certified that error appears in the above-identified patent and that said Letters Patent is hereby corrected as shown below:

Title page,
Item 62], Related U.S. Application Data, should read:
-- Division of application no. 09/117,154, filed on Jul. 24, 1998, now abandoned, which is a 371 of International Application No. PCT/GB97/00226, filed January 24, 1997. --.

Signed and Sealed this

Seventeenth Day of August, 2004

JON W. DUDAS
*Acting Director of the United States Patent and Trademark Office*